United States Patent
Modi (10) Patent No.: US 7,838,011 B2
(45) Date of Patent: *Nov. 23, 2010

(54) STABILIZED PROTEIN COMPOSITIONS FOR TOPICAL ADMINISTRATION AND METHODS OF MAKING SAME

(76) Inventor: Pankaj Modi, 519 Golf Links Road, Ancaster, Ontario (CA) L9G 4X6

(*) Notice: Subject to any disclaimer, the term of this patent is extended or adjusted under 35 U.S.C. 154(b) by 746 days.

This patent is subject to a terminal disclaimer.

(21) Appl. No.: 11/057,481

(22) Filed: Feb. 14, 2005

(65) Prior Publication Data

US 2006/0182766 A1    Aug. 17, 2006

(51) Int. Cl.
*A61K 39/08* (2006.01)
*A61K 31/74* (2006.01)
*A61K 47/44* (2006.01)
*A23J 1/00* (2006.01)

(52) U.S. Cl. .............. 424/239.1; 424/78.03; 424/284.1; 530/412

(58) Field of Classification Search ................ 424/239.1
See application file for complete search history.

(56) References Cited

U.S. PATENT DOCUMENTS

| 6,585,993 B2 | 7/2003 | Donovan et al. | |
|---|---|---|---|
| 6,638,621 B2 * | 10/2003 | Anderson | 428/402.24 |
| 2003/0118598 A1 * | 6/2003 | Hunt | 424/184.1 |
| 2004/0033254 A1 * | 2/2004 | Song et al. | 424/449 |
| 2004/0247623 A1 | 12/2004 | Cady | |

FOREIGN PATENT DOCUMENTS

| EP | 0319638 A1 | 6/1989 |
|---|---|---|
| EP | 0525167 B1 | 9/1995 |
| EP | 0812186 B1 | 10/2001 |
| WO | WO9101719 A1 | 2/1991 |
| WO | WO 0158472 | 8/2001 |
| WO | WO03015698 A2 | 2/2003 |
| WO | WO 2004/060384 A2 | 7/2004 |
| WO | WO2005046637 A2 | 5/2005 |

OTHER PUBLICATIONS

Carpender et al., Interactions of Stabilizing Additives with Proteins During Freeze-Thawing and Freeze-Drying, International Symposium on Biological Product Freeze-Drying and Formulation, Oct. 24-26, 1990; Karger (1992), 225-239.
Goodnough et al., Stabilization of Botulinum Toxin Type A During Lyophilization, App & Envir. Micro. 58 (10) 3426-3428 (1992).
Schmidt, et al., Endoproteinase Activity of Type A Botulinum Neurotoxin Substrate Requirements and Activation by Serum Albumin, J. of Protein Chemistry, 16 (1),19-26 (1997).

* cited by examiner

*Primary Examiner*—Robert Mondesi
*Assistant Examiner*—Khatol Shahnan-Shah
(74) *Attorney, Agent, or Firm*—Gersten Savage LLP (57) ABSTRACT

A stabilizing composition that also enhances permeation is provided for the topical or transdermal administration of an active ingredient. The composition comprises collagen, elastin, sphingosine and cerebroside. Also provided are pharmaceutical or cosmetic formulations comprising an effective amount of an active agent and the stabilizing composition as well as methods of administering active agents topically or transdermally.

10 Claims, 3 Drawing Sheets

FIG. 1

Western Blot Analysis #1

FIG. 2A

Lane-1 Molecular weight marker

Lane-3 Stabilized Botulinum Toxin (at time 0 month)

Western Blot Analysis (repeat # 2 at 6 months time)

FIG. 2B

Lane-1 Molecular weight marker
Lane- 2 Pure Botulinum Toxin (from vial)
Lane- 3 Stabilized Botulinum Toxin (6 months)

Molecular mass marker ranges from the top represents the molecular weights of 200, 116, 98, 67, 55, 37, 28 and 14 kDa.

Before and After Photographs (Botulinum Toxin Cream)

FIG. 3D

STABILIZED PROTEIN COMPOSITIONS FOR TOPICAL ADMINISTRATION AND METHODS OF MAKING SAME

FIELD OF INVENTION

The present invention relates to methods for stabilizing active ingredients in pharmaceutical compositions to provide a prolonged shelf-life with enhanced availability of active ingredients.

BACKGROUND OF THE INVENTION

For storage stability and convenience of handling, proteinaceous pharmaceutical compositions are often formulated as a lyophilized (i.e. freeze dried) or vacuum dried powder and stored at low temperatures between −10 C to 4 C. The dry powder is reconstituted with a suitable fluid, such as saline or water, prior to administration to a patient. Alternatively, a proteinaceous pharmaceutical composition can be formulated as an aqueous solution or suspension that includes a stabilizer to prevent protein degradation. However, many proteins are very difficult to stabilize resulting therefore in a loss of protein and/or protein activity during the formulation, reconstitution and/or the period of storage. Stability problems can occur as a result of protein denaturation, degradation, dimerization, and/or polymerization. Various excipients, such as albumin and gelatin have been used with differing degrees of success to try and stabilize a protein active ingredient in a pharmaceutical composition. Cryoprotectants such as alcohols have been used to reduce protein denaturation under the freezing conditions of lyophilization. Stabilizers can work by reducing adhesion of the protein active ingredient to surfaces, such as the surfaces of laboratory glassware, vessels, the vial in which the pharmaceutical composition is reconstituted or the inside surface of a syringe used to inject the pharmaceutical composition. Adhesion of a protein active ingredient to surfaces leads to loss of active ingredient and can also contribute to denaturation of the remaining retained protein active ingredient, both of which reduce the total activity of the active ingredient present in the pharmaceutical composition. Stabilizers can also reduce denaturation of the active ingredient which can occur upon preparation of a low dilution solution of the active ingredient. As well as being able to stabilize a protein in a composition, an ideal stabilizing agent should have negligible immunogenicity when injected into a human patient.

Pure botulinum toxin is so labile that it is has limited practical utility to prepare a pharmaceutical composition. Botulinum toxin complexes, such as the toxin type A complex are extremely susceptible to denaturation due to surface denaturation, heat, and alkaline conditions. Inactivated toxin forms toxoid proteins which may be immunogenic. The resulting antibodies can render a patient refractory to toxin injection. As with enzymes generally, the biological activities of the botulinum toxins is dependent, at least in part, upon their three-dimensional conformation. Additionally, it is known that dilution of the toxin complex obtained by the known culturing, fermentation and purification to the much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Current stabilizers that have been used in botulinum toxin formulations are animal derived albumin and gelatin. However, these stabilizers are not able to sufficiently stabilize botulinum toxin for storage at room temperature. Thus there is a specific need for enhancement of the stability of botulinum toxin and also to promote its permeation through the skin.

The process that leads to skin aging and wrinkles is complex. A primary cause of wrinkling is a build-up of free radical toxic plaque that binds to collagen and elastin fibers, causing the skin's supportive structure to become inflexible and unhealthy. Laugh lines, smile lines, crow's feet or facial creases appear in areas where repeated muscle movement occurs.

In 2002 the FDA approved the Botulinum Toxin Type A (BOTOX® Cosmetic) to temporarily improve the appearance of moderate to severe frown lines between the eyebrows (glabellar lines). BOTOX® Cosmetic is a purified protein produced by the Clostridium botulinum bacterium. The toxin reduces the activity of the muscles that cause frown lines between the brows to form over time. While BOTOX® Cosmetic has been successful in some cases, there are areas where it should not be used, such as throat and neck areas, around the mouth, near the eyes, and the hands. If the muscles in these areas are paralyzed or disabled, it can lead to difficulty talking, smiling, eating, swallowing, moving hands and fingers, and seeing.

Current formulations of BOTOX® Cosmetic must be administered within four hours after reconstitution since the toxin molecule is very labile. During this time period, reconstituted BOTOX® Cosmetic is stored in a refrigerator (4.degree. C.). Breakdown of the toxin into toxoid can induce immune responses to the toxoid that can interfere with subsequent treatments.

Animal derived or donor pool proteins such as gelatin and serum albumin have been used with some success to stabilize botulinum toxin. However, there has been a desire for improved methods of stabilizing botulinum toxins.

It has been suggested that a suitable alternative to human serum albumin as a botulinum toxin stabilizer may be another protein or a low molecular weight (non-protein) compound (Carpender et al., Interactions of Stabilizing Additives with Proteins During Freeze-Thawing and Freeze-Drying, International Symposium on Biological Product Freeze-Drying and Formulation, Oct. 24-26 1990; Karger (1992), 225-239. However, many substances commonly used as carriers and bulking agents in pharmaceutical compositions have proven to be unsuitable as albumin replacements in compositions containing Clostridial toxin. For example, the disaccharide cellobiose has been found to be unsuitable as a botulinum toxin stabilizer. The use of cellobiose as an excipient in conjunction with albumin and sodium chloride was reported to result in a much lower level of toxicity/efficacy (10% recovery) after lyophilization of crystalline botulinum toxin type A with these excipients, as compared to the toxicity after lyophilization with only human serum albumin (>75% to >90% recovery). Goodnough et al., Stabilization of Botulinum Toxin Type A During Lyophilization, App & Envir. Micro. 58 (10) 3426-3428 (1992). Schmidt, et al., Endoproteinase Activity of Type A Botulinum Neurotoxin Substrate Requirements and Activation by Serum Albumin, J. of Protein Chemistry, 16 (1), 19-26 (1997).

Gelatin has been used in some protein active ingredient pharmaceutical compositions as an albumin substitute. However, it does not provide for stabilization of botulinum toxin at room temperature.

Several efforts have been made to provide botulinum toxin formulations that can be stabilized and delivered in alternative ways. For example, U.S. Pat. No. 6,585,993 discloses a biocompatible implant for continuous release of a neurotoxin over a treatment period extending from one month to five years. While such an implantable system may be useful for certain situations, such as for the treatment of migraine, this type of implant system is not feasible for the treatment of facial, neck or hand wrinkles.

United States Patent Application No. 2004/0247623 suggests a method for the treatment of sensory neuron related distorters through transdermal application of a neurotoxin. This application is particularly directed to a method of treating migraine. The application suggests that botulinum toxin can be administered transdermally through a variety of ways. For example, the toxin may be incorporated into a transdermal patch or it may be administered through electrophoresis. The application also suggests that botulinum toxin can be administered using a topical cream. They teach that this would be achieved by reconstituting botulinum toxin with normal saline and then mixing the reconstituted toxin with a suitable cream or base and then massaging it on to the affected area. This type of application is unlikely to have much effect since the reconstituted botulinum toxin will have a very short active life.

International Patent Application WO 0158472 describes a pharmaceutical composition comprising botulinum toxin and a polysaccharide. This application teaches that the polysaccharide stabilizes the neurotoxin. However, other studies, as discussed above, have shown that sacharrides are poor'stabilizers for botulinum toxin.

International Patent Application WO 04/060384 discloses a pharmaceutical botulinum toxin composition which includes a sequestration agent. The purpose of the sequestration agent is to prevent the diffusion of the botulinum toxin away from the site of injection. This does not address the need for stable compositions that can be applied to the surface of the skin.

There is no doubt that BOTOX® Cosmetic can smooth out fine lines and wrinkles for most users. However, there are several disadvantages associated with its use. The BOTOX® Cosmetic must be administered in a doctor's office. The injections can be painful and there may be bruising. Adverse side effects occur in some injection treated patients. Most common side effects for treatment of frown line include droopy eyelids, nausea, flu-like symptoms (fever etc.), headache and respiratory infections. Less frequent reactions may include facial pain, redness at the injection site, and muscle weakness at other sites. Repeated treatments may lead to permanent paralysis of facial muscles leaving the face expressionless.

Thus, there was a need for newer methods for stabilization of botulinum toxin. The present invention addresses that need. There was a further need for an alternative method of administering botulinum toxin that does not involve injections.

SUMMARY OF THE INVENTION

The present invention addresses the need for improved compositions by providing a method for stabilizing large protein active ingredients for storage at room temperature. The invention also provides a composition prepared using the stabilizing method for the transdermal delivery of the active component. One preferred active component according to the present invention is botulinum toxin (MW150 kD).

In one aspect of the invention, a method of stabilizing an active ingredient in a topical composition is provided. The method comprises admixing the active ingredient with sphingosine, cerebroside, collagen and elastin.

A method for making a stabilized active protein agent composition, said method comprising the steps of:
 i. admixing sphingosine and cerebroside;
 ii. dissolving the admixture of step:
  1. in alcohol;
 iii. removing the alcohol;
 iv. adding an aqueous solution of the active protein agent to form an active agent composition; and
 v. admixing the active agent composition with a solution of solubilized collagen and low molecular weight elastin to form a stabilized protein composition.

In a preferred embodiment of the method, the sphingosine and cerebroside are admixed in equal amounts.

In another preferred embodiment, the alcohol is ethanol and it is preferably removed by vacuum evaporation.

In a further preferred embodiment, the active agent composition comprises micelles.

In yet another embodiment, the solution of solubilized collagen and elastin comprises equal amounts of collagen and elastin.

In a preferred embodiment, the active protein agent is botulinum toxin, preferably botulinum toxin Type A, more preferably botulinum toxin in saline.

In a further preferred embodiment, a method for preparing cosmetic or pharmaceutical formulation is provided. According to the method, the stabilized composition is combined with other ingredients to form a cream, lotion, gel, ointment or other formulation that is acceptable for topical administration.

In another aspect of the invention, a composition for transdermal delivery of an active component is provided. The composition comprises the active ingredient together with collagen, elastin and cerebroside. In one preferred embodiment, the active component is botulinum toxin. The botulinum toxin may be botulinum toxin Type A, Type B, Type C, Type D, Type E, Type F or Type G or combinations thereof. In a preferred embodiment, botulinum toxin Type A is used.

In a preferred embodiment, the composition comprises about 1 to 40 wt/wt % of collagen, about 1 to 40 wt/wt % of elastin, about 0.1 to 15% sphingosine and about 0.1 to 15% cerebroside.

In a further preferred embodiment, the composition comprises an agent which enhances the penetration of the botulinum toxin through the dermal layer. This enhancing agent is selected from the group consisting of d-limonene, allantoin, fulvic acid, myrrh, hydroquinone glyquin, quillaja saponaria (QTS), and acanthophyilum squarrusom (ATS).

The compositions of the present invention are preferably formulated into a cream, lotion, gel, ointment or the like for topical administration.

In a further aspect of the invention, a method of treating skin is provided. The method comprises applying the composition described above daily to areas of the skin which are wrinkled or damaged.

The present invention has many advantages over traditional injections with BOTOX® Cosmetic. The composition of the present invention can be safely used in areas such as the throat and neck, around the mouth, near the eyes and on the hands. Another advantage of the present invention is that the composition can be formulated as a cream or lotion and it can be stored at room temperature for extended periods of time without any loss of activity of the active ingredient. Another advantage is that the stabilizing method of the present invention eliminates the need for the use of human serum albumin as a stabilizing agent. Since human serum albumin is a blood derived product, the elimination of this from the product reduces the risk of blood borne diseases being transmitted through an injection. Furthermore, because the stabilizing method keeps the protein stable and reduces the incidence of toxoid formation, there is less likelihood of a patient developing antibodies to the botulinum toxin. In addition, the methods and compositions of the present invention are cost effective and simple to use. For example, the topical composition can be used at home without any costly doctor office visits. It also eliminates the need for painful injections. Rather than one single large dose of botulinum toxin being delivered once to a single site, the methods and compositions of the present invention allow the botulinum toxin to be administered at low dose, daily, to provide an effective treatment with enhanced safety and reduced side effects.

The methods and compositions of the invention have been shown to reduce fine lines and wrinkles, increase the moisture level of the skin, increase skin elasticity and resilience, increase the firmness of the skin, improve skin tone, texture and overall radiance, diminish bags under the eyes, rejuvenate the skin, prevent damage from chemical stress, protect the skin from UV rays and free-radical damage, and remove irregular pigmentation.

BRIEF DESCRIPTION OF THE DRAWINGS

These and other features of the invention will become more apparent from the following description in which reference is made to the appended drawings wherein.

DETAILED DESCRIPTION

Large proteins can be difficult to stabilize in formulations for storage at room temperatures. Therapeutic proteins are often stored lyophilized and reconstituted before use. Alternatively, the protein composition may be kept frozen prior to use. The present invention provides methods for stabilizing large proteins, as well as therapeutic or cosmetic compositions containing proteins as active ingredients. The stabilized compositions of the invention can be stored for extended periods of time at room temperature.

Botulinum toxin is a relatively large protein for incorporation into a pharmaceutical or cosmetic formulation. The molecular weight of botulinum toxin type A complex is 150 kD and due to the large size of the molecule it is fairly fragile and labile. A stabilizer component should be able to interact with the toxin in a manner which does not denature, fragment or otherwise detoxify the toxin molecule or cause disassociation of the toxin complex.

The present invention provides novel stabilization methods and products by using collagen in combination with peripheral low molecular weight soluble elastin. Sphingosine and cerebroside are additional stabilizing components. Botulinum toxin formulated according to the present invention, remained stable and was not denatured or fragmented or detoxified in the formulation at room temperature for period of 6 months (as assessed from the stability data of the 6 months and clinical data).

As used herein, the term "protein stabilizer" or "primary stabilizer" refers to an agent that helps to preserve or maintain the biological structure (i.e. the three dimensional conformation) and/or the biological activity of a protein. Stabilizers can be proteins or polysaccharides. Examples of protein stabilizers include hydroxyethyl starch (hetastarch), gelatin, collagen, or collagen. The primary stabilizer can be a synthetic agent that does not induce an immune response or induces an attenuated immune response in a subject. Additional stabilizers may also be included in a pharmaceutical composition. These additional or secondary stabilizers may be used alone or in combination with primary stabilizers, such as proteins and polysaccharides. Exemplary secondary stabilizers include, but are not limited to non-oxidizing amino acid derivatives (such as a tryptophan derivate, such as Nacetyl-tryptophan ("NAT")), caprylate (i.e. sodium caprylate), a polysorbate (i.e. P80), amino acids, and divalent metal cations such as zinc. A pharmaceutical composition can also include preservative agents such as benzyl alcohol, benzoic acid, phenol, parabens and sorbic acid or a cresol, such as an M-cresol.

As used herein, the term "enhancing agent" refers to an agent that promotes the absorption of an active protein agent by the skin. Examples of enhancing agents include, but are not limited to, alcohols, such as short chain alcohols, long chain alcohols, or polyalcohols, amines and amides, such as urea, amino adds or their esters, amides, AZONE(R)), derivatives of AZONE(R), pyrrolidones, or derivatives of pyrrolidones; terpenes and derivatives of terpenes; fatty acids and their esters; macrocyclic compounds; tensides; or sulfoxides such as, decylmethylsulfoxide. Liposomes; transfersomes; lecithin vesicles; ethosomes; water; surfactants, such as anionic, cationic, and nonionic surfactants; polyols; and essential oils can also function as enhancing agents.

As used herein, the term "topical" is used to refer to administration to the skin. The term "transdermal" is used to refer to penetration through the other layer or stratum corneum of the skin. The term "transdermal delivery" is meant to refer to delivery of an active agent to the muscles underlying the skin. It is not meant to refer to systemic delivery to the circulatory system.

In the methods and compositions of the present invention, collagen is used as a stabilizer. In addition to stabilizing botulinum toxin according to the invention, collagen helps improve the tissue's underlying foundation and contributes to hydration. Collagen is able to penetrate the skin without the aid of any penetration enhancers.

In a preferred embodiment of the invention, elastin is also included. Elastin is a protein that coil and recoils like a spring within the elastic fibers of connective tissue and accounts for the elasticity of structures such the skin, blood vessels, heart, lungs, intestines, tendons, and ligaments. Elastin functions in connective tissue together with collagen. Whereas elastin provides elasticity, collagen provides rigidity to connective tissue. Low-molecular weight elastin is the only elastin complex capable of penetrating the skin without the aid of any penetration enhancers. Collagen and low molecular weight soluble elastin complex in conjunction with Botulinum Toxin A help diminish the appearance of wrinkles.

The compositions and methods of the present invention also include a sphingosine. Sphingolipid or sphingosine-1-phosphate has been recognized as a bioactive molecule involved in the regulation of cell growth, differentiation, survival, and chemotaxis as well as angiogenesis and embryogenesis. Researchers have identified sphingosine-1-phosphate as a potent chemoattractant for keratinocytes as well as an activator of extracellular matrix production by fibroblasts. The other species of Ceramides or sphingolipids are (N-acyl-sphingosine) and dihydroceramide (N-acyl sphinganine).

Galactosylceramide (cerebroside), a metabolite of sphingolipids is also included. Cerebroside is a myelin related protein that plays an important role in the regulation of cell growth, differentiation, survival, and chemotaxis. Cerebroside sulfates are important membrane constituents. Cerebroside is a mild basic or neutral protein.

The stabilizing agents used in the present invention, collagen in combination with peripheral low molecular weight soluble elastin (EBP) and a mixture of sphingosine and cerebroside are non toxic and easy to handle. They provide an effective alternative to albumin and still meet the stringent botulinum toxin containing pharmaceutical composition formulation requirements.

Figure 1:
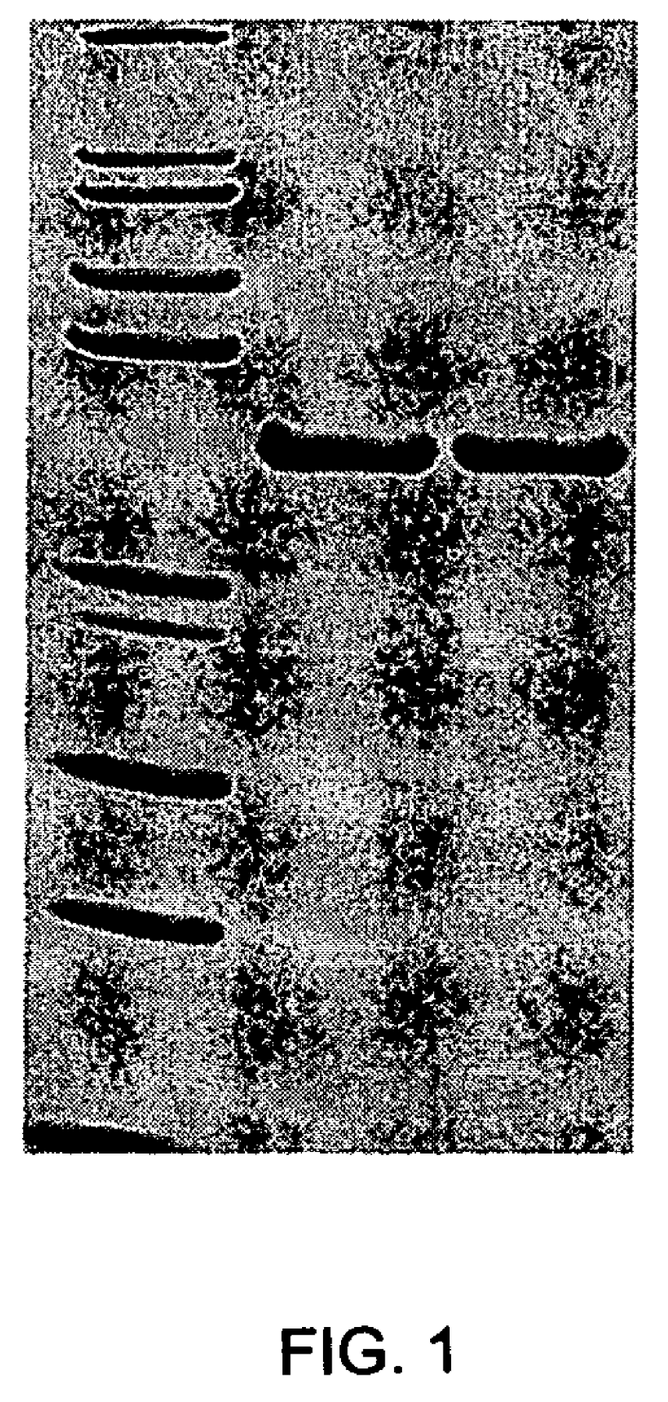
FIG. 1 Illustrates an SDS polyacrylamide gel analysis.
Figure 2A:
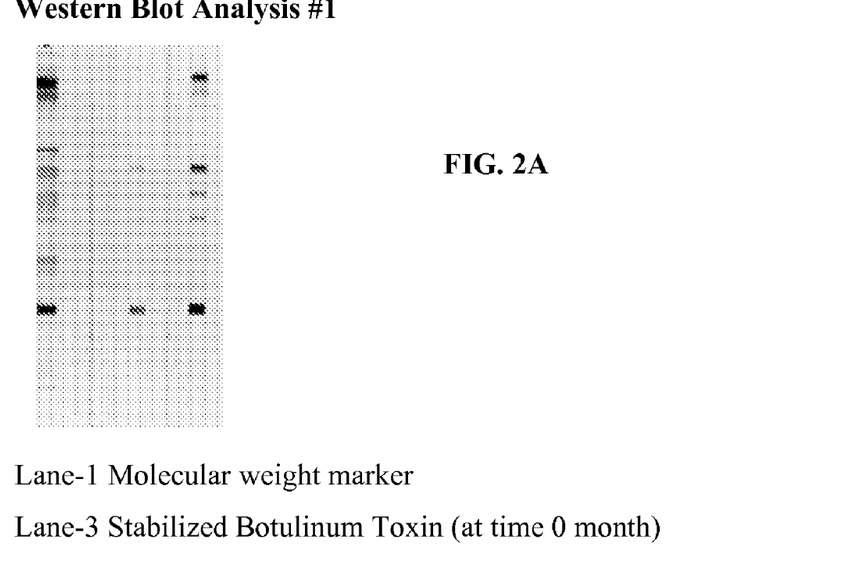
FIGS. 2A and 2B illustrates representative Western Blot analyses of the composition of the invention.
Figure 2B:
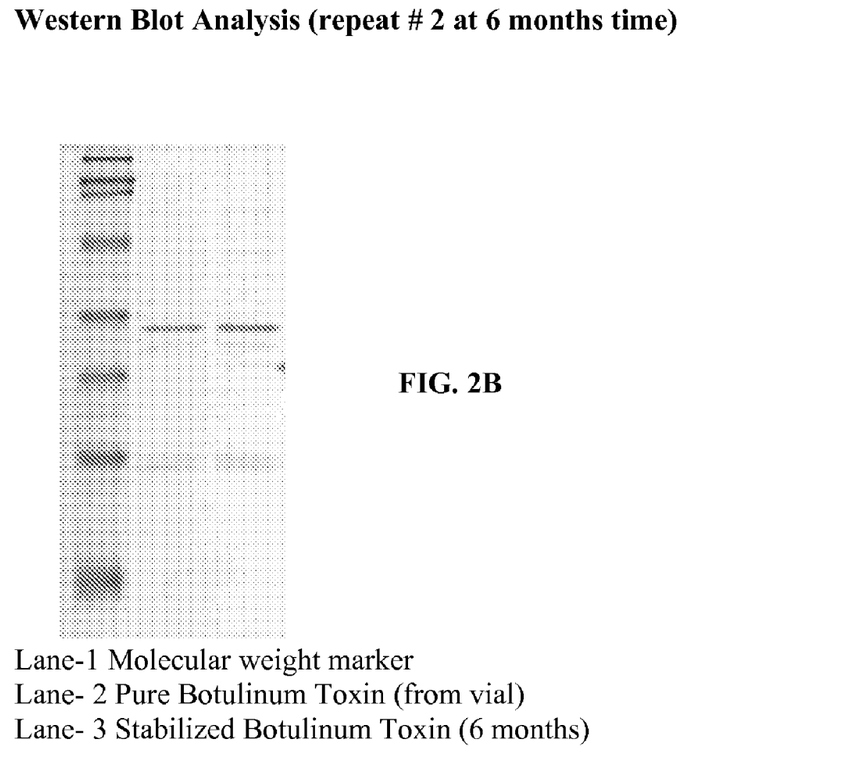
Figure 3A:
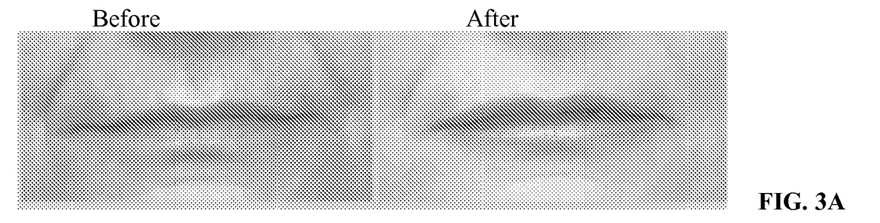
FIGS. 3A to 3D are photographs of patients treated with the composition of the present invention.
Figure 3B:
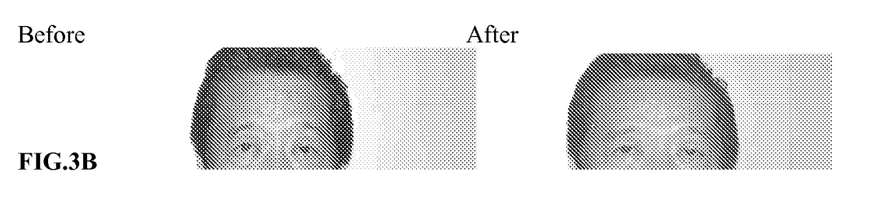
Figure 3C:
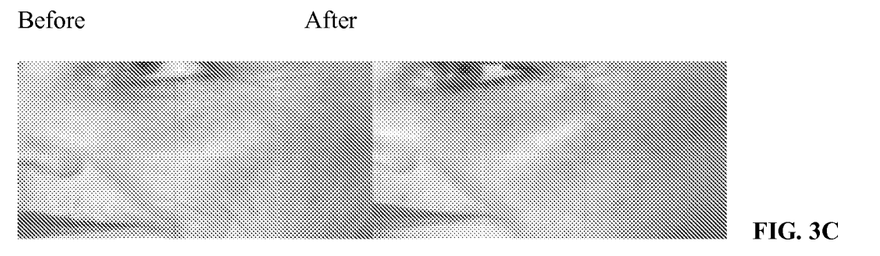
Figure 3D:
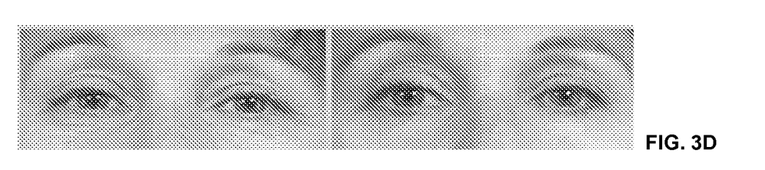

According to one method of the invention, a stabilized protein composition is made by combining collagen and low molecular weight elastin in a solvent, such as saline. In a separate flask, sphingosine and cerebroside are dissolved in an alcohol, preferably ethanol. The alcohol is then removed, for example by rotary vacuum evaporation. This results in a coating of sphingosine and cerebroside on the flask. A solution containing the protein to be stabilized is added to the flask. This preferably results in the formation of micelles of sphingosine, cerebroside and protein. This micellar composition is added to the mixture of collagen and elastin and stirred. This stabilized composition can then be stored at room temperature. Further details of an exemplary composition can be found in Example 1 below. The method of the present invention was used to stabilize the protein, botulinum toxin. FIGS. 1 and 2 illustrate SDS-PAGE and Western blots of compositions of stabilized botulinum toxin.

Botulinum toxin type A consists of a toxin molecule of about 150 kD in noncovalent association with nontoxin proteins weighing about 750 kD. The nontoxin proteins are believed to preserve or help stabilize the secondary and tertiary structures upon which toxicity is dependant. The stabilization technique of the present invention based on the use of collagen in combination with elastin-binding protein (EBP) and mixture of sphingosine and cerebroside maintains the integrity of the complex without denaturing or fragmentation or detoxification. Thus, the invention provides a novel method for stabilizing botulinum toxin.

A further advantage is that proteins like collagen, elastin and sphingomyelins are non-immunogenic.

In addition to having enhanced stability, the compositions of the present invention may include components that enhance absorption through the skin. Thus, the compositions can be formulated into a topical composition such as a cream, lotion, gel, ointment, spray or mask. As a cream, lotion or gel, and by way of example only, about 0.5 ml to about 20 ml or more may be used on a human subject's face, depending on the area to be treated and at least to some extent, the severity of the affliction to be treated. The composition may also be included in make-up formulations such as foundations or lip balm.

The following may be included to enhance absorption/penetration of botulinum toxin through the thick dermal layers. These agents are approved by the FDA for human use and are on the GRAS (generally recognized as safe) list of the FDA. These agents do not interact chemically with botulinum toxin. These additives not only enhance absorption botulinum toxin through the skin layers but they also aid in the stability preservation because of their neutral nature and antioxidant properties.

In one aspect of the invention d-limonene is included in the composition to enhance penetration of the toxin through the dermal layer. Limonene was found to be an effective enhancer at 0.30%, enhancing skin permeation of botulinum toxin Type A approximately fourfold.

In one preferred embodiment of the invention, allantoin is included in the preparation. Allantoin is a substance which triggers new cell formation, shrinks damaged tissues and stimulates the penetration of collagen. The FDA OTC Panel has recognized Allantoin as a skin protectant and a mild neutral permeation enhancer.

In another preferred embodiment, fulvic acid is included in the preparation. Fulvic acid is a low molecular weight antioxidant. It enhances the body's absorption of drugs through the transdermal route without any side effects.

Myrrh is a further optional ingredient in the skin cream preparation of the invention. Myrrh is a gum resin extracted from Arabian and Somolian shrubs that helps soothe inflamed tissues and rejuvenate skin, hair, and nails.

Eldopaque or HYDROQUINONE Glyquin may also be included. It is used to lighten the dark colored patches of skin (also called melama, liver spot, age spots, freckles) caused by birth control pills, hormone medicine, injury to the skin, or simply aging. It may be included together with sunscreen to help prevent these spots from reoccurring due to sunlight or UV light exposure.

Quillaja saponaria (QTS) and Acanthophyllum squarrusom (ATS) total saponins are two natural enhancers that may also be included. They demonstrate moderate activity as skin penetration enhancers. These compounds may also be included in a skin cream or lotion of the present invention.

The enhancing agents may be included at various stages of the process. For example, they may be added to the stabilized composition at the same time as the micellar composition is added to the collagen and elastin mixture. Preferably, the enhancing compounds are introduced during the formulation of the stabilized composition into a pharmaceutical or cosmetic formulation. The preparation of an exemplary formulation for topical application is described in Example 3 below.

The present invention provides a composition that is capable of delivering a botulinum toxin through a person's skin. The composition contains an enhancing agent that facilitates the permeation of the botulinum toxin through the patient's skin. The composition is suitable for topical administration whereby the composition penetrates the skin and transdermally denervates an underlying muscle. The composition may be provided on a patch that is adhesively secured to the skin so that the toxin can pass from the patch through the skin to denervate an, underlying muscle. Compositions containing botulinum toxin and an enhancing agent can be used to successfully treat several types of disorders associated with neurotransmitter release when applied to a person's skin. Examples of disorders amenable to treatment by the topical administration of the compositions set forth here in include, and are not limited to, wrinkles, such as brow furrows, headaches, such as migraine, headache pain, cervical dystonia, focal hand dystonia, neurogenic inflammation, hyperhydrosis, blepharospasm, strabismus, hemifacial spasm, eyelid disorder, cerebral palsy, focal spasticity, limb spasticity, tics, tremors, bruxism, anal fissure, fibromyalgia, dysphagia, lacrimation, and pain from muscle spasms. The compositions disclosed herein provide localized relief via delivery of botulinum toxin.

The compositions and formulations of the invention are useful to reduce the signs of aging. Clinical trials were conducted using a topical cream formulation containing botulinum toxin. Details of the trial can be found in Example 4 below. As can be clearly seen from the before and after photographs in FIG. 3, topical administration of stabilized botulinum toxin cream significantly reduces the signs of aging.

In another aspect of the invention, a pharmaceutical or cosmetic formulation is provided containing an effective amount of an active agent and an effective amount of the stabilizing enhancing composition, and a pharmaceutically acceptable carrier suitable for topical or transdermal administration. The formulation may be in any form suitable for application to the skin. For example, it may take the form of a cream, a lotion, a gel, an ointment, a paste, or a solution. The formulation may include lipozone, micelles, or microspheres. The formulation may be: a cosmetic composition that includes in addition to the stabilizers and the active ingredients water and other additives that are normally used in cosmetics. For example, it may include thickening agents, preservatives, emulsifiers, perfumes, dyes or coloring, vegetable or mineral oil, antiseptic agents, acidifying or alkalizing agents, vitamins, anti-UV agents, surfactant, solvents, pH stabilizing agents, and other active ingredients known to be effective on the skin. The cosmetic composition may be provided as a milk, cream, lotion, serum, mask or gel. The cosmetic composition may also be provided as skin foundation, lip balm, etc.

While the description has focused on transdermal delivery of botulinum toxin, it is clearly apparent that the stabilizing and enhancing composition can be used to deliver other active agents transdermally. Examples of active agents that can be delivered in the way include, but are not limited to androgens, androstenediol and androisoxazole (for anabolic disorders), testosterone (hypogonadism, muscle wasting, male impotence, postmenopausal symptoms in women), dihydrotestosterone (hypogonadism, muscle wasting), dehydroepiandrostenone (muscle wasting, fat reduction, fitness); estrogens (postmenopausal symptoms, birth control), 17 betaestradiol, estradiol-3,17-diacetate, estradiol-3-acetate, estradiol-17-acetate, estradiol-3,17-valerate, estradiol-3-valerate, estradiol-17-valerate, ethinyl estradiol, estrone; progesterones (prevent endometriosis, prevent endometrial cancer, control habitual abortion, suppress or synchronize estrus, promote hair growth), progesterone (preg-4-ene-3,20-dione), norethindrone, norgestrieone, norgestadienone, norgestrel, norgestimate, progestogenic acid, dihydroprogesterol, nomagesterol. The testosterone hormone may be used in any of its usual forms, such as, acetate, propionate, 17-beta-cyclopentanepropionate, enanthanate, isobutyrate, undeconate, and the like. Similarly, the estradiols may additionally be used in any of the known or newly developed forms, such as, for example, pivalate, propionate, cypionate, benzoate and other esters. Other drugs such as insulin, insulin like growth factors, vaccines, peptides like GLP, IGF, heparin, hirugen, hirulos, huridine, mumps, measles and rubella vaccine, typhoid vaccine, hepatitis A vaccine, hepatitis B vaccine, herpes simplex virus, bacterial toxoids, cholera toxin B-subunit, influenza vaccine virus, bordetala pertussis, vaccinia virus, adenovirus, canary pox, polio vaccine virus, plasmodium falciparum, bacillus calmette geurin (BCG), klebsiella pneumoniae, HIV envelop glycoproteins, bovine somatropine, estrogens, androgens, insulin growth factors, interleukin-I, interleukin-II and cytokins, small molecule drugs such as NSAJD, narcotics, etc. may be delivered using the compositions of the present invention.

Botulinum Toxin A can be stabilized using the methods of present invention and the stabilized toxin can be successfully delivered transdermally to achieve similar results to those obtained by intramuscular injection of BOTOX® Cosmetic. The formulation can be applied all over the face and neck and hands as opposed to a BOTOX® Cosmetic injection which is targeted primarily to areas around eyes and the forehead to reduce the wrinkle.

The present invention has been described with regard to one or more embodiments. However, it will be apparent to persons skilled in the art that a number of variations and modifications can be made without departing from the scope of the invention as defined in the claims.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Example 1

Preparations

Botulinum toxin (BOTOX® Cosmetic) vials were reconstituted of sterile saline solution (0.9%). The vials were shaken vigorously to dissolve the botulinum toxin (BOTOX® Cosmetic). The reconstituted vials were kept refrigerated and were utilized within 1 hour of reconstitution.

In a round bottom flask of 50 mL capacity, 10 mg of soluble collagen and 10 mg of Elastin were combined. The mixture was solubilized in 10 mL of sterile saline solution (0.9%) with continuous stirring. In a separate 50 mL round bottom flask, 5 mg of sphingosine and 5 mg cerebroside were combined. This mixture was dissolved in pure ethanol. The alcohol was completely removed by rotary vacuum evaporation to obtain a uniform coating of the sphingosine and cerebroside on the flask wall. To this flask 800 units of botulinum toxin solution in 6 ml of (0.9%) saline was added. The flask was swirled and then stirred continuously for 5 mins at room temperature to uniformly coat the botulinum toxin with the sphingosine and cerebroside micelle coating to prevent degradation. This coated and preserved micellar botulinum toxin solution was then added to the flask containing the mixture of collagen and cross linked low molecular weight elastin. The solution was stirred for about 5 mins slowly and then kept at a room temperature in a brown glass vial.

Example 2

SDS-PAGE and Western Blot Analysis

The stability of the preserved botulinum toxin (Botox) solution was analyzed by standard analytical techniques using SDS-PAGE and Western Blot analysis and HPLC analysis at time zero (few minutes after the preparation of the coated stabilized solution) and thereafter every month in comparison with the uncoated Botox solution.

SDS-PAGE was performed in all cases under reducing conditions with a BIO-RAD® mini-cell apparatus (Bio-Rad Laboratories, Calif.) with 10% precast tricine gels. The botulinum toxin neat (pure sample diluted with saline) was loaded in one lane as the comparator to the stabilized botulinum toxin which was loaded in the second lane. Both columns were loaded with approximately 100 units of the toxin. The loading buffer, tank buffer, and the molecular weight markers were obtained from Bio-Rad Laboratories. The protein bands were visualized by the Coomassie blue staining technique. Protein concentration (density) from SDS polyacrylamide gels was measured with a BIO-RAD® densitometry system and analyzed with the standard imaging software analyzer. The comparison of the Botulinum Toxin A bands, i.e. the neat botulinum toxin without stabilization and the stabilized botulinum toxin revealed no degradation in the stabilized botulinum toxin which was kept at a room temperature for 6 months. The results are shown in FIG. 1.

Western blot analysis For Western blot analysis, proteins separated on SDS-polyacrylamide gels were transferred to the nitrocellulose membranes at 25 V for 60 mm with a BIO-RAD® protein blot module. After the complete transfer of the protein from the gel, the protein binding sites on the membranes were blocked by incubation at room temperature in 5% skim milk-Tris-buffered saline (TBS) for 60 mm. Membranes were then incubated at a room temperature with affinity-purified MAb produced against the botulinum toxin (gift from the local University Biotechnology Dept) at 5 µg/ml in 5% skim milk-TBS for 4 hrs. After several washes with TBS buffer, the membranes were incubated at room temperature with affinity-purified goat anti-mouse IgG (Sigma-Aldrich, Co.) at 4 .mu.g/ml in 5% skim milk-TBS buffer for 3 hrs. After another four to five washes with the TBS buffer, the membranes were incubated with TMB [3,3', 5,5'-tetramethylbenzidine] membrane substrate (Bio-Rad Laboratories) until color developed. This analysis revealed that after 6 months time period the botulinum toxin at room temperature was stable and was not degraded and denatured to loose its potency. The results of two exemplary Western Blots are shown in FIGS. 2A and 2B.

Example 3

Cream Formulation

The stabilized botulinum toxin composition was formulated into a cream for topical administration as outlined below.

| Total Volume of the cream (400 mL) | |
|---|---|
| Phase A: | |
| De-ionized Water | 74.7% |
| Tetra Sodium EDTA | 0.5-0.7% |
| Methyl Paraben | 0.2% |
| Propylene Glycol | 3.0%-4.0% |
| Glycerin | 3.0%-4.0% |
| Phase B: | |
| Cetyl Alcohol (Ado 1 52 NE) | 2.0% |
| Cetearyl Alcohol | 2.0% |
| Glyceryl Stearate | 2.0% |
| PEG-100 Stearate | 1-2% |
| Stearic Acid (Emersol 132) | 4.5% |
| Sorbitan Palmitate | 0.5-0.7% |
| Polysorbate-85 | 1.0% |
| Polysorbate 60 | 0.5-1% |
| Lanolin Alcohol (Ritachol) | 1.0% |
| HoHoba Oil | 0.5-1% |
| Lanolin | 1-2% |
| Tocopheryl Acetate | 0.5-1% |
| Dimethicone 200 | 0.7-1.0% |
| BHA | 0.1% |
| Propylparaben | 0.1% |
| Diazolidinyl UREA | 0.2% |
| Phase C: | |
| Fragrance (lilac, jasmine) | as needed |
| Aloe Vera (powder) | 1.5%-2.0% |
| CoQ-10 | 0.5% |
| Retinyl A | 0.03-0.05% |
| Hyaluronic Acid (pure) | 1.0-1.5% |
| Talcum Powder (Ti02) | 1.0-1.5% |

| -continued | |
|---|---|
| Total Volume of the cream (400 mL) | |
| Phase D: | |
| d-limonene | 0.7% |
| Allantoin | 0.5% |
| Fulvic Acid | 0.5% |
| Quillaja saponaria (QTS) | 0.3% |
| Acanthophyllum squaimsom (ATS) | 0.3% |
| Myrrh Extract | 0.2% |
| Hydroquinone Glyquin | 4.0% |
| Phase E: | |
| Stabilized Botulinum Toxin in Collagen Matrix | 800 units |

Procedure:

Heat Phase A and Phase B separately with agitation to 75 C. Add Phase A to Phase B and mix 30 minutes at 75 C. Cool down to 20-22 C and then add Phase C, D and E and continue to agitate until homogenous and one phase.

Example 4

Clinical Studies in Human Subjects

The effectiveness of the stabilized botulinum toxin (Botox) was tested using a cream formulation. Human subjects with wrinkles applied the cream for a period of month or more. The subjects were photographed before and after one month of the application of the cream on their face.

The clinical guidelines established by Allergan to test their Botox injection was followed for the testing of the effectiveness of the stabilized formulation in healthy subjects (male and female) age range from 40-75 years.

Botulinum Toxin Type A was not present in the peripheral blood at measurable levels following the dermal application of the cream at the low doses of 1.7 units per mL of the cream. Each cream vial contained 50 units of Botox in 30 ml of cream. The recommended quantities of neurotoxin administered at each treatment (in the morning and at the bed time) did not result in systemic, adverse clinical effects, i.e. muscle weakness, in patients without other neuromuscular dysfunction.

Clinical Studies: Assessment of the Glabellar Lines

A randomized, single-center, double blind, placebo-controlled (placebo cream contained all the ingredients except the Botox), parallel-group study was conducted to evaluate the effectiveness of the stabilized Botox cream of the invention for use in the temporary improvement of the appearance of moderate to severe Glabellar facial lines. The study enrolled 40 healthy adult patients (ages 40 to 75 years, female or male) with Glabellar lines of at least moderate severity at maximum frown. Patients were excluded if they had an infection or skin problems, history of facial nerve palsy, marked facial asymmetry, ptosis, excessive dermatochalasis, deep dermal scarring, thick sebaceous skin, inability to substantially lessen glabellar lines even by physically spreading them apart or had a known history of neuromuscular disorder or other disorder that could interfere with neuromuscular function. Subjects were asked to apply the actual stabilized Botox cream twice a day (once in the morning and at the bed time) for a month. The subjects were instructed to wash their face with warm water and soap thoroughly to remove any sweat, dirt, and oils from their faces. They were instructed apply the stabilized Botox cream or placebo cream around their eyes, forehead, and neck or on the wrinkled skin areas with the supplied applicator so as to avoid any contamination of the product by hand. All subjects were examined prior to the beginning of the study by a qualified dermatologist and were declared healthy and fit to enter in the study. They were photographed by an expert photographer prior to the beginning of the study. All subjects were asked to follow their normal daily routine without any restriction and asked to live their normal life style.

The primary efficacy measurements were the investigator's rating of glabellar line severity at maximum frown at Day 30 post-treatment and the subject's global assessment of change in appearance of glabellar lines at Day 30 post-treatment. For the investigator rating, a photoguide was provided to each study center to assist in grading the severity of glabellar lines using a 4-point grading scale (0=none 1=mild 2=moderate 3=severe). A responder was defined as having a severity grade of 0 or 1. For the global assessment of change in appearance of glabellar lines, the subject responded to the question, "How would you rate the change in the appearance of your glabellar lines compared with immediately before your treatment with the non-invasive Botox cream?" The ratings of responses by subjects were from +4 (complete improvement, about 100%) to −4 (very marked worsening, about 100% worse or greater). A responder was defined as having a grade of at least +2 (moderate improvement, about 50%).

A secondary efficacy endpoint was the investigator's rating of glabellar line severity at rest at Day 30 post-treatments in those subjects who at baseline demonstrated a glabellar line severity score at rest of moderate or severe. For the investigators' rating, the criteria for effectiveness was a 30 percentage point difference between the stabilized Botox cream and placebo treatment groups in the incidence of subjects with an investigator's rating of glabellar line severity of none or mild at maximum frown. For the subjects' rating, the criteria for effectiveness was a 25 percentage point difference between the stabilized Botox cream and placebo treatment groups in the incidence of subjects with a score of at least +2 (moderate improvement) in subject's global assessment of change in the appearance of glabellar lines.

The combined results are presented here. There were 40 subjects (20 subjects in the actual Botox cream treated group and 20 subjects in the placebo cream treated group) who had glabellar line severity scores at rest of moderate or severe.

The mean age was 54 years, with a range of 40 to 74 years. Of this, majorities were ☐50 years of age and 6.0% were ☐65 years of age. Most of the subjects were female, 80% (32/40) and Caucasian, 83.8%.

In these studies, the severity of glabellar lines was reduced in less than 7 days in the Botox cream group compared to the placebo cream group as measured both by investigator rating of glabellar line severity at maximum frown and at rest, and by subject's global assessment of change in appearance of glabellar lines. By Day 10, 80% (16/20) of subjects had achieved a severity score of mild at maximum frown by the investigator's assessment. This increased to 92% by the primary efficacy endpoint day of Day 30, compared to placebo-treated patients (Table 1). By Day 10, 84% of subjects in the active group assessed moderate or better improvement in their own appearance (+2 or better). This increased to 93% by the primary efficacy endpoint day of Day 30, compared to 3% of placebo-treated patients. Based on resting appearance as judged by the investigator, 62% of subjects achieved a severity score of none or mild at Day 11, and 94% by the efficacy endpoint day of Day 30.

TABLE I

| Day | Botox-Cream | Placebo | Difference | p-Value |
|---|---|---|---|---|
| 7 | 76% (15/20) | 3% (1/20) | 73% | <0.0001 |
| 10 | 80% (16/20) | 3% (1/20) | 77% | <0.0001 |
| 20 | 88% (18/20) | 5% (1/20) | 83% | <0.0001 |
| 30 | 94% (19/20) | 5% (1/20) | 89% | <0.0001 |

The actual results can be seen in the photographs of FIGS. 3A to 3D.

What is claimed is:

1. A stabilized protein composition, said composition comprising: an active protein agent, collagen, elastin, one or more absorption enhancers selected from a groups consisting of short chain alcohols, long chain alcohols, or polyalcohols, amines and amides, and at least one active agent encapsulated in a phospholipid micelle formed by the combination of surfactants, solvents and stabilizers and wherein said protein composition is stabile at room temperature for a period of time in excess of four weeks.

2. A stabilized protein composition according to claim 1, wherein the absorption enhancer is selected from the group consisting of d-limonene, allantoin, fulvic acid, myrrh, hydroquinone glyquin, quillaja saponaria (QTS), and acanthophyllum squarrusom (ATS).

3. A composition according to claim 1, wherein the active protein agent is botulinum toxin wherein the botulinum toxin is stable at room temperature for at least six months.

4. A composition according to claim 3, wherein the active protein agent is botulinum toxin Type A.

5. A pharmaceutical or cosmetic formulation comprising a composition as defined in claim 1 and at least one additive suitable for topical administration.

6. A pharmaceutical or cosmetic formulation according to claim 1 comprising:
an active protein agent;
approximately 1 to 40% wt collagen;
approximately 1 to 40% wt elastin;
approximately 0.1 to 15% sphingosine phospholipid; and
approximately 0.1 to 15% cerebroside phospholipid.

7. A formulation according to claim 5, wherein the active agent is botulinum toxin.

8. A formulation according to claim 7, wherein the botulinum toxin is Type A.

9. A composition according to claim 2, wherein the active protein agent is botulinum toxin wherein the botulinum toxin is stable at room temperature for at least six months.

10. A composition according to claim 6, wherein the active protein agent is botulinum toxin wherein the botulinum toxin is stable at room temperature for at least six months.

* * * * *